United States Patent
Wahl et al.

(10) Patent No.: US 8,118,849 B2
(45) Date of Patent: Feb. 21, 2012

(54) BONE SCREW WITH SELECTIVELY SECURABLE WASHER

(75) Inventors: Rebecca Hawkins Wahl, Escondido, CA (US); Hanspeter Robert Bayer, Meriden, CT (US); Ronald George Litke, Jr., Danbury, CT (US); Scott W. Reed, Monroe, CT (US); Alan G. Taylor, Memphis, TN (US)

(73) Assignee: Tornier, Inc., Edina, MN (US)

( * ) Notice: Subject to any disclaimer, the term of this patent is extended or adjusted under 35 U.S.C. 154(b) by 485 days.

(21) Appl. No.: 11/724,530

(22) Filed: Mar. 15, 2007

(65) Prior Publication Data
US 2007/0233125 A1    Oct. 4, 2007

Related U.S. Application Data

(60) Provisional application No. 60/783,759, filed on Mar. 17, 2006.

(51) Int. Cl.
*A61B 17/04* (2006.01)
*A61B 17/86* (2006.01)
*A61F 2/08* (2006.01)

(52) U.S. Cl. ........ 606/315; 606/305; 606/306; 606/316; 606/317; 606/319

(58) Field of Classification Search .......... 606/62, 606/75, 73, 105, 315, 314, 319, 290, 305, 606/306, 232, 307, 308, 324; 411/533, 539
See application file for complete search history.

(56) References Cited

U.S. PATENT DOCUMENTS

| | | | |
|---|---|---|---|
| 2,779,375 A * | 1/1957 | O'Connor | 411/134 |
| 5,702,445 A | 12/1997 | Branemark | |
| 6,319,000 B1 * | 11/2001 | Br.ang.nemark | 433/75 |
| 6,319,254 B1 * | 11/2001 | Giet et al. | 606/916 |
| 6,685,707 B2 * | 2/2004 | Roman et al. | 606/916 |
| 6,730,093 B2 * | 5/2004 | Saint Martin | 606/303 |
| 6,953,463 B2 | 10/2005 | West, Jr. | |
| 2003/0105465 A1 | 6/2003 | Schmieding et al. | |
| 2004/0106925 A1 * | 6/2004 | Culbert | 606/73 |

(Continued)

OTHER PUBLICATIONS

Kmi—Kinetikos Medical Incorporated webpage http://visitkmi.com, KMI the Small Bone Specialist, Kompressor Compression Screw System, Mar. 10, 2006.

(Continued)

*Primary Examiner* — Thomas C. Barrett
*Assistant Examiner* — Andrew Yang
(74) *Attorney, Agent, or Firm* — Faegre Baker Daniels LLP (57) ABSTRACT

A screw assembly (10) for insertion into a bone region (12A) (12B) includes a screw body (14) and a washer (16). The screw body (14) includes a distal end (218), a proximal end (224), and a distal threaded area (220), and a proximal threaded area (226). The distal threaded area (220) is positioned near the distal end (218) and the proximal threaded area (226) is positioned near the proximal end (224). The washer (16) includes a washer threaded area (238) that engages the proximal threaded area (226) to selectively secure the washer (16) to the screw body (14). With this design, the washer (16) can be selectively attached to the screw body (14) and different sized washers (16) can be alternatively and selectively secured to the screw body (14). As a result thereof, the person inserting the screw assembly (10) can pick the washer (16) size best suited to retain the bone region (12A) (12B) in which the screw assembly (10) is being inserted.

16 Claims, 11 Drawing Sheets

U.S. PATENT DOCUMENTS

2006/0116686 A1* 6/2006 Crozet .......................... 606/73

OTHER PUBLICATIONS

Wright Charlotte™ High-Demand Compression Screws Surgical Technique Brochure 2005.

Synthes®, 6.5. mm and 7.3 mm Cannulated Screws Technique Guide ©2003.

Search Report and Written Opinion for PCT/US2007/066656 (related to the present application), publication date Dec. 14, 2007, Rebecca Hawkins Wahl et al.

International Preliminary Report on Patentability and Written Opinion for PCT/US2007/006656 (related to the present application), publication date Oct. 2, 2008, Nexa Orthopedics, Inc. (now assigned to Tornier, Inc. on Feb. 29, 2008).

* cited by examiner

BONE SCREW WITH SELECTIVELY SECURABLE WASHER

RELATED APPLICATION

This application claims priority on U.S. Provisional Patent Application Ser. No. 60/783,759 filed on Mar. 17, 2006 and entitled "BONE SCREW WITH SELECTIVELY SECURABLE WASHER". The contents of U.S. Provisional Application Ser. No. 60/783,759 are incorporated herein by reference.

BACKGROUND

It is often necessary to fuse two bone regions to repair a fracture or to fuse a joint. One type of device used to fuse two bone regions is a bone screw. An example of a bone screw that is commonly utilized in joints or other areas where flexibility is important is a compression screw, which allows for greater flexibility in the area where the two bone regions have been fused, while still maintaining maximum stability and control. Sometimes the two bone regions being fused may contain poor bone stock due to osteoporosis or other bone abnormalities.

SUMMARY

The present invention is directed toward a screw assembly for insertion into a bone region. The screw assembly includes a screw body and a washer. In one embodiment, the screw body includes a distal end, a proximal end, and a distal threaded area. The distal threaded area is positioned near the distal end. The washer engages the proximal end of the screw body to selectively secure the washer to the screw body.

With this design, in certain embodiments, the washer is designed to be selectively attached to the screw body and different sized washers can be alternatively and selectively secured to the screw body. As a result thereof, the person inserting the screw assembly can pick the washer size best suited to the bone region in which the screw assembly is being inserted.

A number of alternative designs are provided herein. In one embodiment, the screw body includes a proximal threaded area is positioned near the proximal end. In this embodiment, the washer can include a washer threaded area that engages the proximal threaded area to selectively secure the washer to the screw body. For example, the proximal threaded area can include an externally threaded surface and the washer threaded area can include an internally threaded surface. With this design, the washer can be selectively threaded and locked onto the screw body.

In certain embodiments, the proximal threaded area has a PTA length that is greater than a washer thickness of the washer. With this design, when the washer is selectively locked onto the proximal threaded area, a portion of the proximal threaded area is exposed for engaging the bone region.

In one embodiment, the proximal threaded area includes a threaded BT region that engages the bone region, and a threaded WT region that is engaged by the washer threaded area. In this embodiment, the BT region has a different thread pitch than the WT region. As a result thereof, the washer can be threaded onto the WT region until the washer is urged against the BT region.

In one embodiment, the washer can be initially slipped over the distal end and threaded onto the proximal end. In another embodiment, the washer includes a washer slit that allows the washer to be initially slipped from the side of the screw body onto an intermediate region of the screw body. In yet another embodiment, the screw body can include reverse threads and the washer can be threaded onto the proximal end from the back side of the screw body.

In certain embodiments, the washer can include washer teeth that can cut into the bone region to further secure the washer to the bone region. Additionally, or alternatively, the washer can include a washer fill region that provides an area for bone growth.

As provided herein, in certain embodiments, the screw can be a headless screw that is cannulated or non-cannulated.

In one embodiment, at least one of the screw body and the washer includes a tapered area so that the washer fixedly engages the screw body. For example, the screw body can include a proximal tapered area positioned near the proximal end. Further, in this embodiment, the washer can include a washer tapered area that engages the proximal tapered area to selectively secure the washer to the screw body.

The present invention is also directed to a screw assembly that includes a screw body and a washer combination. In this embodiment, the washer combination includes a first washer having a FW outer diameter and a second washer having a SW outer diameter that is larger that the FW outer diameter. Further, in this embodiment, each of the washers can be alternatively and selectively secured to the screw body near the proximal end. As a result thereof, the person inserting the screw assembly can pick the washer size best suited to retain the bone region in which the screw assembly is being inserted.

Additionally, the present invention is directed to a method for securing a bone region. The method can include the steps of (i) providing a screw body including a distal end, an opposed proximal end, a distal threaded area positioned near the distal end, (ii) fixedly securing a washer to the screw body near the distal end; and (iii) inserting the screw body into the bone region.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 4A is a perspective view.

FIG. 6A is a perspective view, and FIG. 6B is an exploded perspective view of still another embodiment of a screw assembly having features of the present invention;

FIG. 9A is a perspective view, FIG. 9B is an end view, FIG. 9C is a side view.

DESCRIPTION

Figure 1:
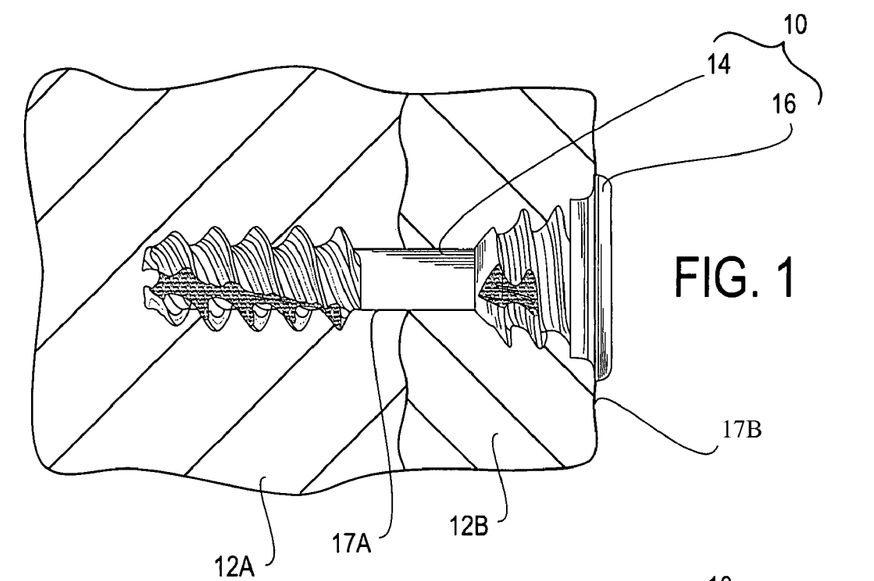
FIG. 1 is a simplified side illustration of a pair of bone regions, in cut-away, that are fused together with a compression screw assembly having features of the present invention.

FIG. 1 is a simplified side illustration of a screw assembly 10 having features of the present invention, a first bone region 12A and a second bone region 12B of a human. In this embodiment, the screw assembly 10 is used to urge the bone regions 12A, 12B together so that the bone regions 12A, 12B are fused together. The type and location of the bone regions 12A, 12B urged together can vary. For example, the screw assembly 10 can be used to fuse a fracture of a human bone, to immobilize and fuse a human joint, or to fuse together adjacent bones. Alternatively, for example, one or more screw assemblies 10 can be used to secure a plate (not shown) or other device to one or more bone regions 12A, 12B.

Although the Figures provided herein illustrate the use of a compression screw as part of the present invention, this is done merely for convenience and is not done to demonstrate that the present invention is only applicable to compression screws. Alternatively, the present invention is equally applicable for use with other types of bone screws for insertion in bone regions.

The screw assembly 10 includes a screw body 14 and a washer 16. The screw body 14 is threaded into one or more of the bone regions 12A, 12B, after a pilot hole 17A has been created in the one or more bone regions 12A, 12B. For example, the screw body 14 can be engaged by an insertion tool such as a wire driver, a drill, or a screwdriver, to facilitate rotation of the screw body 14 and insertion of the screw body 14 into the pilot hole 17A in the one or more bone regions 12A, 12B. Additionally, it should be noted that the screw body 14 can be inserted without the pilot hole, depending upon the condition and type of the one or more bone regions 12A, 12B. In one embodiment, the screw assembly 10 is self tapping.

The washer 16 is designed to be selectively attached to the screw body 14. The washer 16 can be utilized when the adjacent bone region, (e.g. the second bone region 12B in FIG. 1) is comprised of poor quality bone stock. Poor quality bone stock can occur due to osteoporosis or some other type of bone abnormality. The washer 16 can provide a compressive force on the bone region. In certain embodiments, the washer 16 is designed to at least in part be mounted flush with an outside surface 17B of the adjacent bone region (e.g. the second bone region 12B in FIG. 1) into which the screw assembly 10 is being inserted so as to provide additional stability to compensate for the poor quality bone stock.

The design and size of the screw body 14 and the washer 16 can vary according to the desired use and/or the needs of the screw assembly 10.

Figure 2A:
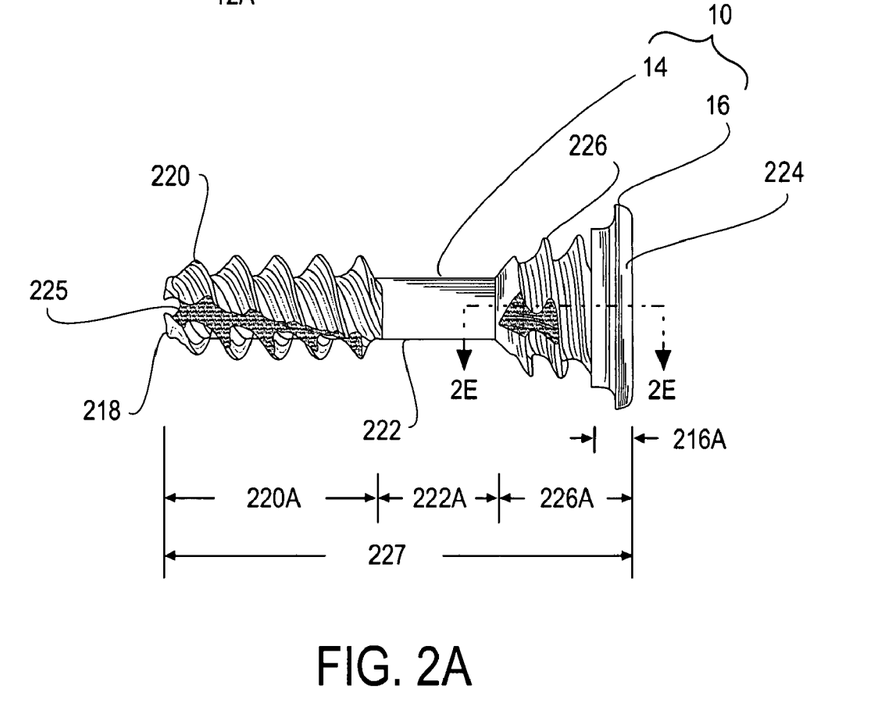
FIG. 2A is a side view of the screw assembly of FIG. 1.

FIG. 2A illustrates a side view of the screw assembly 10 of FIG. 1. The size, shape, and design of the screw assembly 10 can vary according to the teachings provided herein to meet the design requirements of the screw assembly 10. As provided above, the screw assembly 10 includes the screw body 14 and the washer 16. In this embodiment, the screw body 14 is generally circular cylinder shaped and has a generally circular shaped cross-section. In one embodiment, the screw body 14 is integrally formed as a unitary structure. Alternatively, portions of the screw body 14 can be separately formed and joined together during manufacturing. The type of material utilized in the screw body 14 can be varied to meet the requirements of the bone regions 12A, 12B (illustrated in FIG. 1) being fused. For example, the screw body 14 can be formed from titanium, stainless steel, or a bio-absorbable material.

The screw body 14 includes a distal end 218, a distal threaded area 220 positioned adjacent to the distal end 218, a non-threaded area 222, a proximal end 224 opposed to the distal end 218, and a proximal threaded area 226 positioned adjacent to the proximal end 224. The distal end 218 is the portion of the screw body 14 that is initially inserted into the one or more bone regions 12A, 12B. Additionally, the distal threaded area 220 can include a distal slot 225 that facilitates threading of the screw body 14 into the bone regions 12A, 12B.

The design, shape, and size of the screw body 14 can be varied pursuant to the teachings provided herein. Alternatively, for example, the screw body 14 could be designed without one or more of the areas described above. For example, the screw body 14 could be designed without the non-threaded area 222. In alternative, non-exclusive embodiments, the screw body 14 has a SB length 227 of approximately 5, 10, 20, 30, 50, 70, 90, 120, or 150 millimeters. However, greater or lesser SB lengths 227 can be utilized.

The design, location, and length of the distal threaded area 220 can vary to suit the insertion requirements for the screw assembly 10. In FIG. 2A, the distal threaded area 220 extends from the distal end 218 to the non-threaded area 222. In alternative, non-exclusive embodiments, the distal threaded area can have a distal thread length 220A of approximately 5, 10, 15, 20, 30, or 40 millimeters. However, greater or lesser lengths can be utilized. Further, in one embodiment, the distal threaded area 220 has one or more threads that spiral around the perimeter of the screw body 14. For example, the distal threaded area 220 can have a thread pitch of approximately 0.11 inches. However, greater or lesser thread pitches can be utilized for the distal threaded area 220.

Additionally, in FIG. 2A, the distal end 218 and the distal threaded area 220 are tapered to facilitate self tapping of the screw assembly 10 into the one or more bone regions 12A, 12B. In one non-exclusive embodiment, the distal end 218 has a taper of approximately thirty degrees. Alternatively, the distal end 218 and the distal threaded area 220 can have another suitable configuration.

In FIG. 2A, the non-threaded area 222 is relatively small and generally cylindrical shaped. In alternative, non-exclusive embodiments, the non-threaded area 222 has a diameter of approximately 0.18 inches. However, greater or lesser diameters can be utilized.

The design, location, and length of the proximal threaded area 226 can vary to suit the utility requirements for the screw assembly 10. In FIG. 2A, the proximal threaded area 226 extends from the non-threaded area 222 to the proximal end 224. In alternative, non-exclusive embodiments, the proximal threaded area 226 can have a PTA length 226A of approximately 0.3, 0.4, 0.5, 0.6, or 0.7 millimeters. However, greater or lesser lengths can be utilized. Further, in one embodiment, the proximal threaded area 226 is an externally threaded region having one or more threads that spiral around the perimeter of the screw body 14. For example, the proximal threaded area 226 can have a thread pitch of approximately 0.18 inches. However, greater or lesser thread pitches can be utilized for the proximal threaded area 226.

It should be noted that in the embodiment illustrated in FIG. 2A, that the pitch and diameter of the proximal threaded area 226 is different, e.g. greater than the pitch and diameter of the distal threaded area 220. With this design, the screw body 14 urges the bone regions 12A, 12B together during insertion of the screw body 12.

The washer 16 is selectively secured to the screw body 14. With this design, the washer 16 can be fixedly secured to the screw body 14 and does not move relative to the screw body 14 after it is secured to the screw body 14. As a result thereof, the washer 16 is better able to provide additional stability to compensate for the poor quality bone stock. It should be noted that with the present invention, a number of different sized washers 16 can be selectively secured to the screw body 14. With this design, the person installing the screw assembly 10 can select the washer 16 size that best suits the need to provide additional stability while minimizing the size of the washer 16.

It should be noted that the washer 16 has a washer thickness 216A. In one embodiment, the washer thickness 216A is less than the PTA length 226A. In alternative, non-exclusive embodiments, the washer thickness 216A is approximately 10, 50, 100, 200, 300, or 500 percent less than the PTA length 226A. As a result thereof, a portion of the proximal threaded area 226 is exposed after the washer 16 is attached. These exposed proximal threads can engage the bone region 12B to urge the bone regions 12A, 12B together.

Figure 2B:
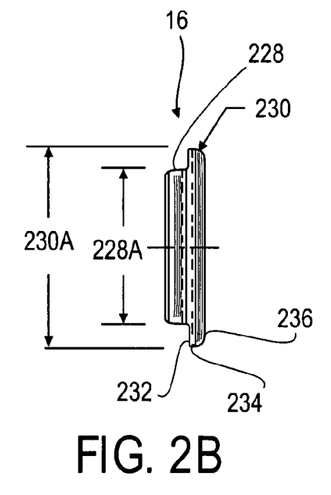
FIG. 2B illustrates a side view of the washer.
Figure 2C:
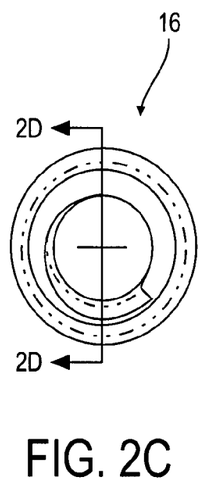
FIG. 2C illustrates an end view of the washer.
Figure 2D:
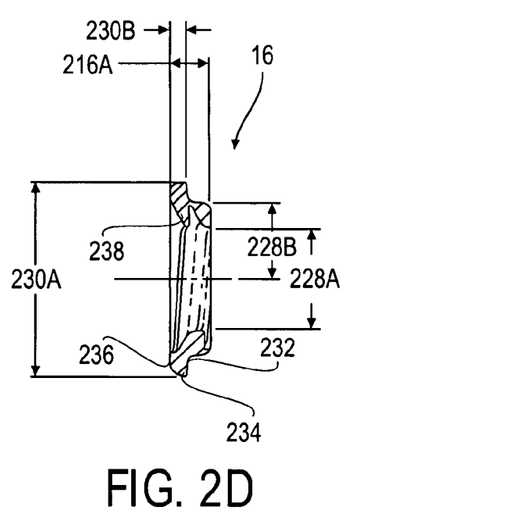
FIG. 2D illustrates a cut-away view of the washer 16 taken on line 2D-2D in FIG. 2C.

FIG. 2B illustrates a side view of the washer 16, FIG. 2C illustrates an end view of the washer 16, and FIG. 2D illustrates a cut-away view of the washer 16 taken on line 2D-2D in FIG. 2C. In this embodiment, the washer 16 includes a first section 228 and a second section 230. The first section 228 has a generally circular ring shaped cross-section, and has a FS outer diameter 228A. In one embodiment, the FS outer diameter 28A is only slightly larger than the diameter of the proximal threaded area 226 so that the first section 228 extends slightly into the adjacent bone region 12B. Additionally the outer diameter of the first section 228 can be slightly tapered 228B to facilitate insertion into the adjacent bone region 12B.

The second section 230 also has a generally circular ring shaped cross-section and it cantilevers out away from the first section 228 so that a SS outer diameter 230A of the second section 230 is greater than the FS outer diameter 228A of the first section 228. The second section 230 includes an interior surface 232, a side surface 234, and an exterior surface 236. In one embodiment, the interior surface 232 is designed to be mounted flush with the outside surface 17A of the adjacent bone region 12B so as to provide additional stability to compensate for poor quality bone stock. The second section 230 extends generally radially outward. The second section 230 can extend outward a very small amount or a fairly large amount depending on the requirements of the screw assembly 10 and the condition of the adjacent bone region 12B. The side surface 234 is rounded toward the exterior surface 236, and the exterior surface 236 is a substantially flat planar surface so as to minimize any irritation to the soft tissue surrounding the bone region 12B. The second section 230 can have a relatively thin SS thickness 230B to minimize the exposed profile of the washer 16.

As illustrated in FIG. 2D, the washer 16 includes an internally threaded washer threaded area 238. The washer threaded area 238 is sized and shaped to interact with the proximal threaded area 226 (illustrated in FIG. 2A) so that the washer 16 can be screwed down securely over the proximal threaded area 226 adjacent to the proximal end 224 of the screw body 14. The proximal threaded area 226 and the washer threaded portion 238 are sized and shaped to provide a secure fit between the two. For example, the proximal threaded area 226 can be tapered so that movement of the washer 216 towards the proximal end 224 causes the washer threaded area 238 to fixedly engage the proximal end of the proximal threaded area 226 to lock the washer 16 to the screw body 14. Further, the washer 16 is threaded from the distal end towards the proximal end of the proximal threaded area 226.

Figure 2E:
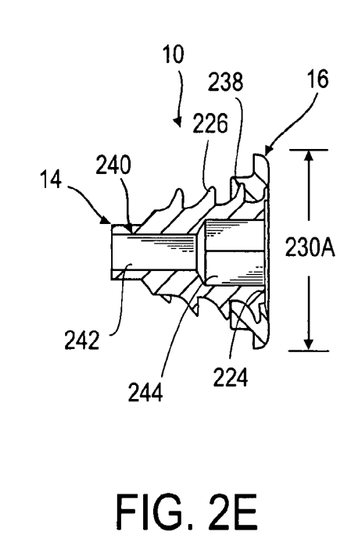
FIG. 2E is a cut-away view taken on line 2E-2E from FIG. 2A.

FIG. 2E is a cut-away view of a portion of the screw assembly 10 taken on line 2E-2E in FIG. 2A. FIG. 2E illustrates that the washer 16 has been threaded on the screw body 14 and that the washer threaded area 238 engages and interacts with the proximal threaded area 226 to fixedly secure the washer 16 to the screw body 14.

It should be noted that after the washer 16 is threaded onto the proximal threaded area 226, a portion of the proximal threaded area 226 is still exposed. As a result thereof, the proximal threaded area 226 can be threaded into the adjacent bone region 12B to further secure the screw assembly 10 to the bone regions 12A, 12B and the proximal threaded area 226 can be used to further compress the bone regions 12A, 12B together.

As illustrated in FIG. 2E, the screw body 14 further includes an aperture 240 that extends through the length of the screw body 14. The aperture 240 allows for the insertion of a guide wire or other elements into the pilot hole 17A within the bone regions 12A, 12B. The aperture 240 includes a first aperture section 242 and a second aperture section 244. The first aperture section 242 is substantially tubular in shape and has a substantially circular cross-section. The first aperture section 242 extends from the distal end 218 (illustrated in FIG. 2A) of the screw body 14 to near the proximal end 224 of the screw body 14. The second aperture section 244 is positioned adjacent to the first aperture section 242 and extends from the first aperture section 242 to the proximal end 224 of the screw body 14. The second aperture section 244 can have a hexagonal cross-section that is designed to receive the insertion tool that is utilized for inserting the screw body 14 within the bone regions 12A, 12B. Alternatively, the second aperture section 244 can be designed with a different shaped cross-section depending upon the requirements of the screw assembly 10 and the shape of the insertion tool.

Figure 2F:
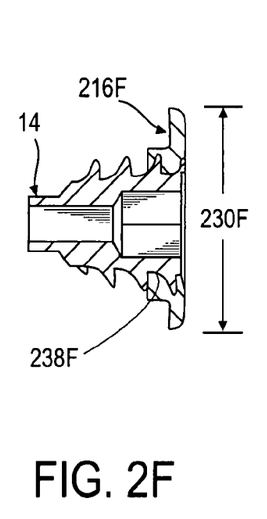
FIGS. 2F and 2G are alternative cut-away views of a portion of the screw assembly.
Figure 2G:
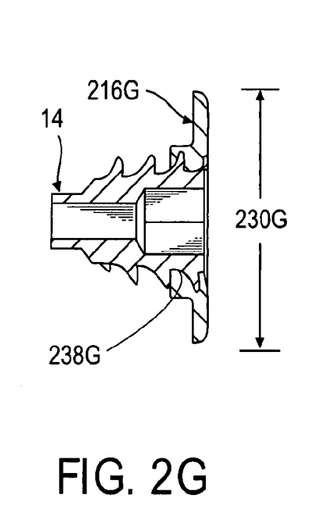

FIGS. 2F and 2G are alternative cut-away views the screw assembly 10 of FIG. 2E. However, in FIG. 2F, a larger diameter washer 216F has been threaded onto the screw body 14 and the larger diameter washer 216F has the washer threaded area 238F that is same as the washer threaded area 238 of FIG. 2E. Somewhat similarly, in FIG. 2G, a even larger diameter washer 216G has been threaded onto the screw body 14 and the even larger diameter washer 216G has the washer threaded area 238G that is same as the washer threaded area 238 of FIG. 2E. With this design, a number of different sized washers 16, 216F, 216G can be selectively and alternatively secured to the screw body 14. With this design, the person installing the screw assembly 10 can interchangeably select the washer 16, 216F, 216G size that best suits the need to provide additional stability for the adjacent bone region 12B while minimizing the size of the washer 16. The number of different sized washers 16, 216F, 216G can vary. For example, the screw assembly could be designed with more than three or less than three alternatively sized washers 16, 216F, 216G. Further, the amount of different in SS outer diameter 230A, 230F, 230G between the washers 16, 216F, 216G can vary. For example, SS outer diameter 230A, 230F, 230G can increase in interval of 10, 20, 30, 50, 100, 200 percent.

It should be noted that the washers 16, 216F, 216G illustrated in FIG. 2E, 2F, 2G can respectively be referred to as the first washer 16, the second washer 216F, and the third washer 216G. Further, the first washer 16 has a first washer diameter 230A, the second washer 216 has a second washer diameter 230F that is greater than the first washer diameter 230A, and the third washer 316 has a third washer diameter 230G that is greater than the first washer diameter 230A, and the second washer diameter 230F.

Figure 3A:
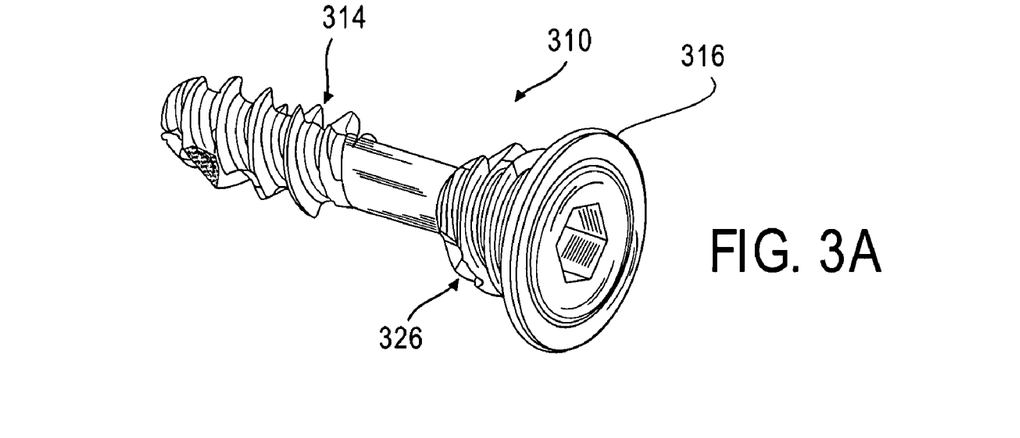
FIG. 3A is a perspective view of a second embodiment of a screw assembly having features of the present invention.
Figure 3B:
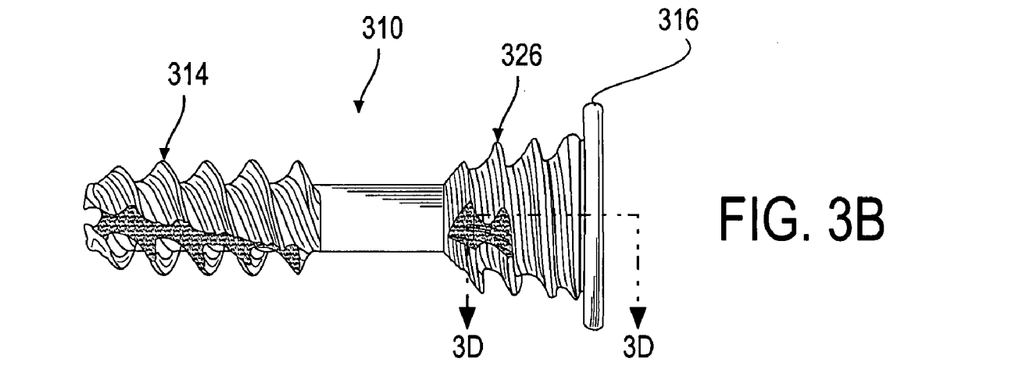
FIG. 3B is a side view of the screw assembly of FIG. 3A.

FIGS. 3A and 3B illustrate a perspective view and a side view, respectively, of a second embodiment of a screw assembly 310 having features of the present invention. The size, shape, and design of the screw assembly 310 can vary according to the teachings provided herein to meet the design requirements of the screw assembly 310.

Similar to embodiment described above, the second embodiment includes the screw body 314 and the washer 316 that are somewhat similar to the embodiments describe above. However, in this embodiment, the proximal threaded area 326 is slightly different and the shape of the washer 316 is slightly different.

Figure 3C:
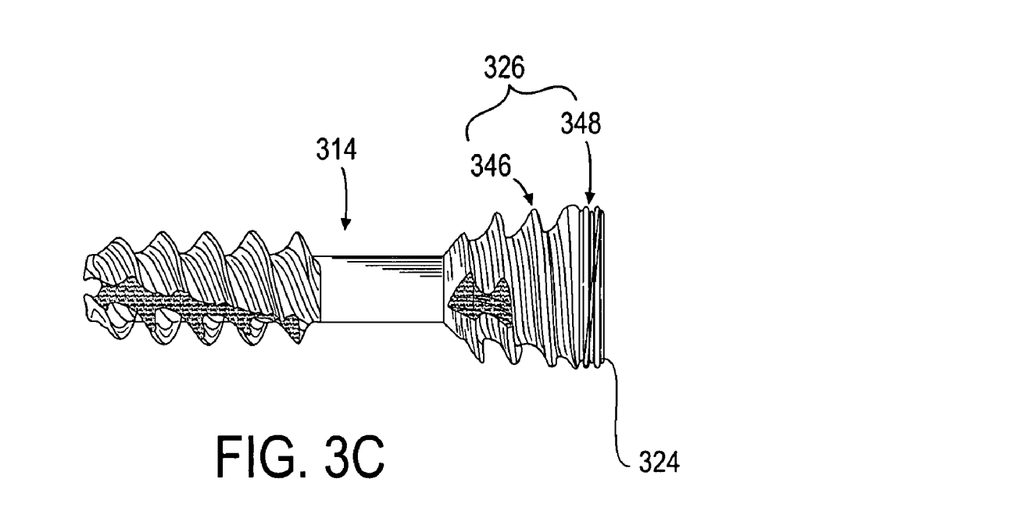
FIG. 3C is a side view of a screw body.

FIG. 3C is a side view of the screw body 314 including the proximal threaded area 326. In this embodiment, the proximal threaded area 326 includes a BT region 346 that is positioned near, but not adjacent to the proximal end 324, and a WT region 348 positioned between the BT region 346 and the proximal end 324. In this embodiment, each of the regions 346, 348 are externally threaded and the threads of the BT region 346 are different than the threads of the WT region 348. Further, the threads of the BT region 346 are designed to engage the adjacent bone region 12B to urge the bone regions 12A, 12B together and secure the screw body 314 to the bone regions 12A, 12B. Moreover, the threads of the WT region 348 are sized, shaped and designed to engage the washer threaded area 338 of the washer 316.

In one embodiment, the threads of the WT region 348 are the opposite of the threads of the BT region 346. In FIG. 3C, the threads of the WT region 348 are reverse threads. With this design, the washer 316 can be threaded onto the screw body 314 from the proximal end 324.

Figure 3D:
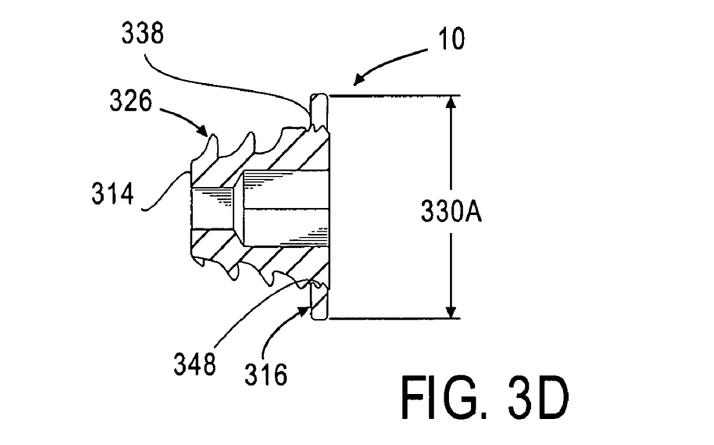
FIG. 3D is a cut-away view taken on line 3D-3D of FIG. 3B.

FIG. 3D is a cut-away view of a portion of the screw assembly 310 taken on line 3D-3D in FIG. 3B. FIG. 3D illustrates that the washer 316 has been threaded on the screw body 314 and that the washer threaded area 338 engages and interacts with the WT region 348 of the proximal threaded area 326 to fixedly secure the washer 316 to the screw body 314. In this embodiment, the washer 316 is threaded from the proximal end 324 towards the distal end 318 until the washer 316 butts against the BT region 346 to lock the washer 316 onto the screw body 314.

It should be noted that after the washer 316 is threaded onto the proximal threaded area 326, the BT region 346 is still exposed and can be threaded into the adjacent bone region 12B.

Figure 3E:
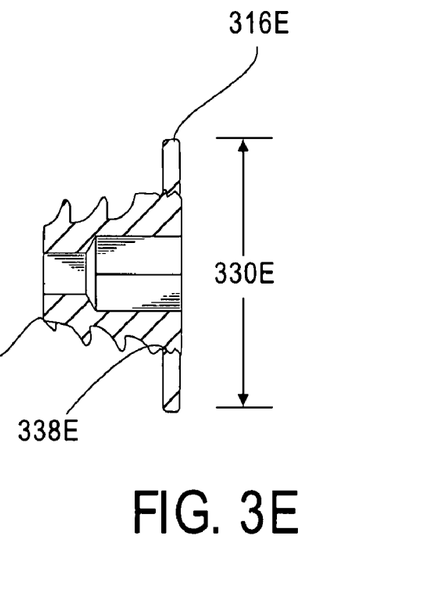
FIGS. 3E and 3F are alternative cut-away views of a portion of the screw assembly.
Figure 3F:
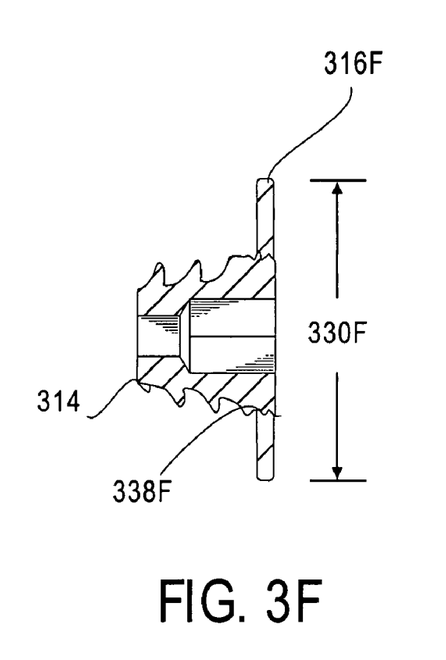

In FIG. 3D, the washer 316 is generally annular disk shaped. Further, washer 316 has a SS outer diameter 330A that is larger than the diameter of the screw body 314. Further, the screw assembly 10 could be designed with a plurality of alternatively sized washers 316 that can alternatively be selectively secured to the screw body 314. In particular, FIGS. 3E and 3F are alternative cut-away views of the screw assembly 10 of FIG. 3D. However, in FIG. 3E, a larger diameter washer 316E has been threaded onto the screw body 314 and the larger diameter washer 316E has the washer threaded area 338E that is same as the washer threaded area 338 of FIG. 3D. Somewhat similarly, in FIG. 3F, a even larger diameter washer 316F has been threaded onto the screw body 314 and the even larger diameter washer 316F has the washer threaded area 338F that is same as the washer threaded area 338 of FIG. 2D. With this design, a number of different sized washers 316, 316E, 316F can be selectively and alternatively secured to the screw body 314. With this design, the person installing the screw assembly 310 can interchangeably select the washer 316, 316E, 316F size that best suits the need to provide additional stability for the adjacent bone region 12B while minimizing the size of the washer 316.

Figure 4A:
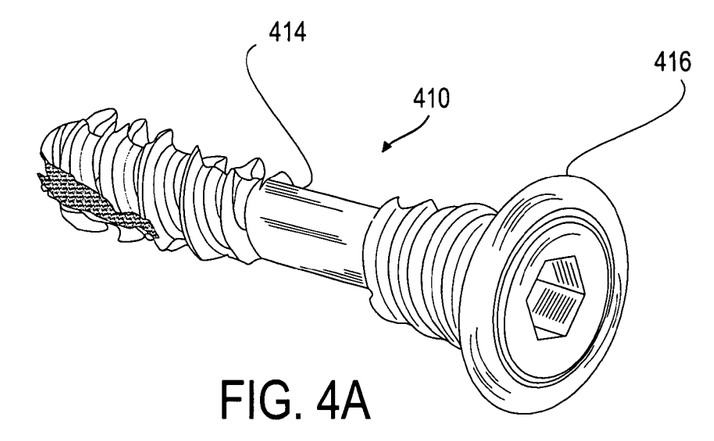
Figure 4B:
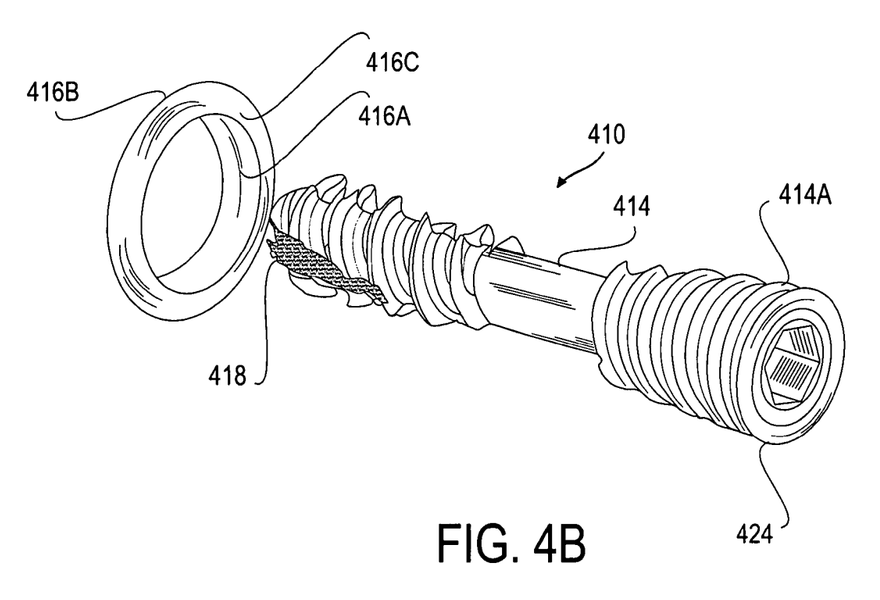
FIG. 4B is an exploded perspective view of another embodiment of a screw assembly having features of the present invention.

FIG. 4A is a perspective view and FIG. 4B is an exploded perspective view of another embodiment of a screw assembly 410 having features of the present invention. In this embodiment, the screw assembly 410 includes a screw body 414 and a washer 416 that are somewhat similar to the corresponding components described above. However, in this embodiment, the screw body 414 includes a proximal tapered area 414A and the washer 416 includes a washer tapered area 416A (instead of threads) that engages the proximal tapered area 414A to fixedly secure the washer 416 to the screw body 414. With this design, the washer 416 can be initially positioned over the distal end 418 and moved towards the proximal end 424 until the washer 416 is taper locked on the screw body 414. For example, the outer diameter of the screw body 414 at the proximal tapered area 414A can increase towards the proximal end 424 and inner diameter of the washer tapered area 416A can increase from a back side 416B of the washer 416 to a front side 416C (e.g. the side of the washer that faces the proximal end 424). Alternatively, the screw assembly 410 could be designed so that only one of the screw body 414 or the washer 416 was tapered.

Figure 5:
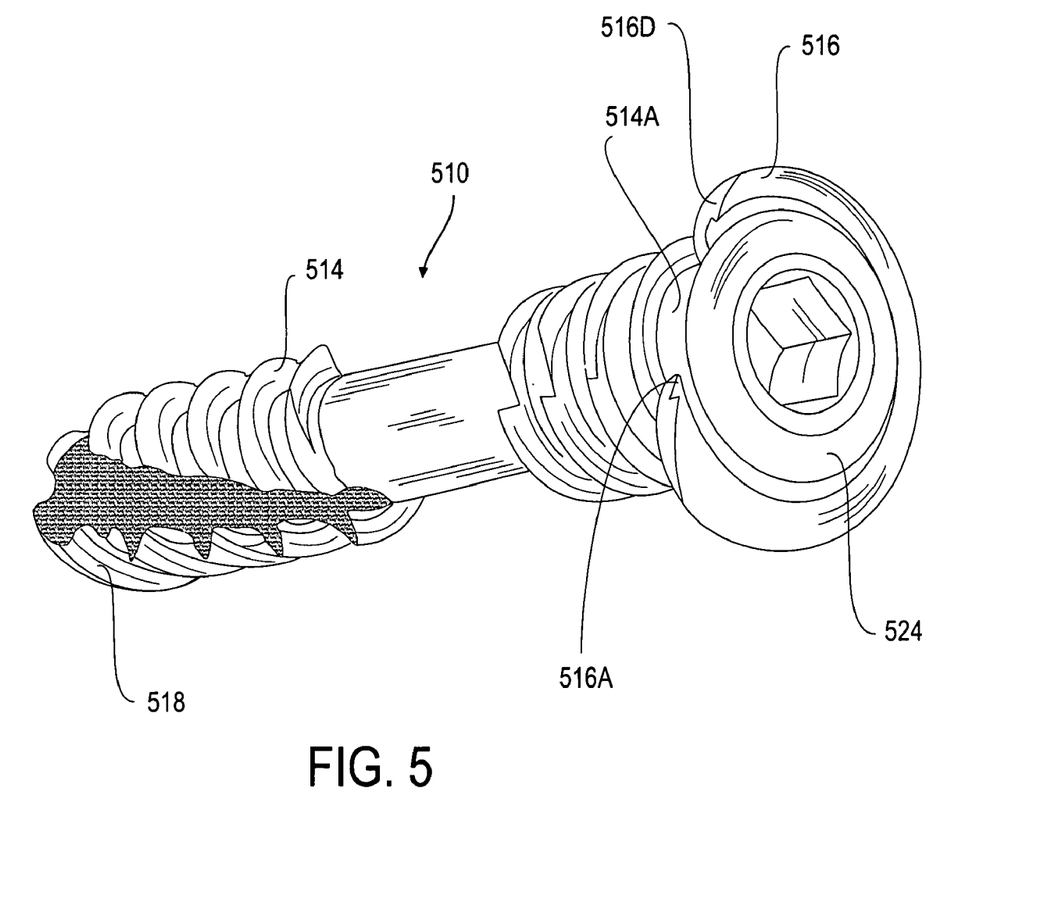
FIG. 5 is a perspective view of yet another embodiment of a screw assembly having features of the present invention.

FIG. 5 is a perspective view of another embodiment of a screw assembly 510 having features of the present invention. In this embodiment, the screw assembly 510 includes a screw body 514 and a washer 516 that are somewhat similar to the corresponding components described above and illustrated in FIGS. 4A and 4B. In this embodiment, the screw body 514 includes the proximal tapered area 514A and the washer 516 includes the washer tapered area 516A (instead of threads) that engages the proximal tapered area 514A to fixedly secure the washer 516 to the screw body 514. However, in this embodiment, the washer 516 is a split type washer that includes a washer slit 516D that allows the washer 516 to be positioned on the screw body 514 from the side of the screw body 514 intermediate the distal end 518 and the proximal end 524. With this design, the washer 516 can be positioned on the screw body 514 after the screw body 514 has been partly inserted into the bone region (not shown in FIG. 5). Additionally, in this embodiment, the washer 516 can be rotated until the washer slit 516D is positioned in the desired location relative to the bone region to have the lowest profile and/or to minimize trauma.

Figures 6A, 6B:
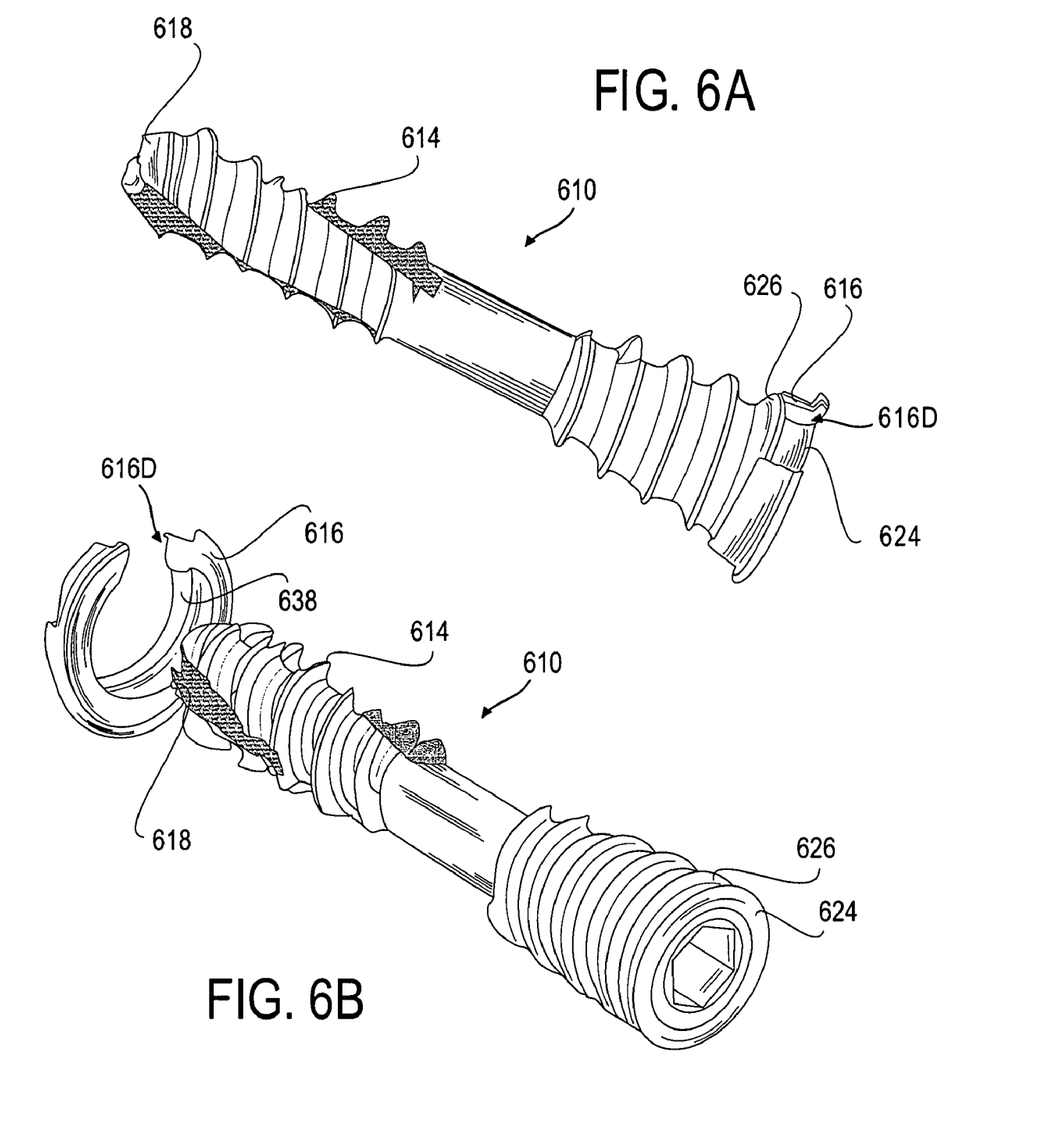

FIG. 6A is a perspective view, and FIG. 6B is an exploded perspective view of still another embodiment of a screw assembly 610 having features of the present invention. In this embodiment, the screw assembly 610 includes a screw body 614 and a washer 616 that are somewhat similar to the corresponding components described above and illustrated in FIG.

5. However, in this embodiment, the washer 616 includes the washer threaded area 638 that engages the proximal threaded area 626 to fixedly secure the washer 616 to the screw body 614. Further, in this embodiment, the washer 616 is a split type washer that includes a washer slit 616D that allows the washer 616 to be positioned on the screw body 614 from the side of the screw body 614 intermediate the distal end 618 and the proximal end 624.

Figure 7A:
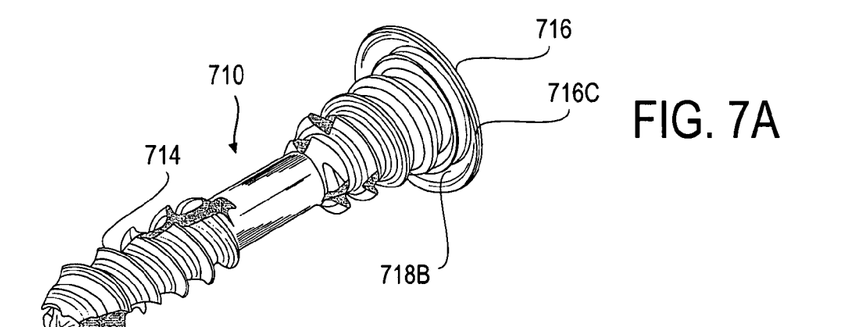
FIGS. 7A and 7B are alternative perspective views of another embodiment of a screw assembly having features of the present invention.
Figure 7B:
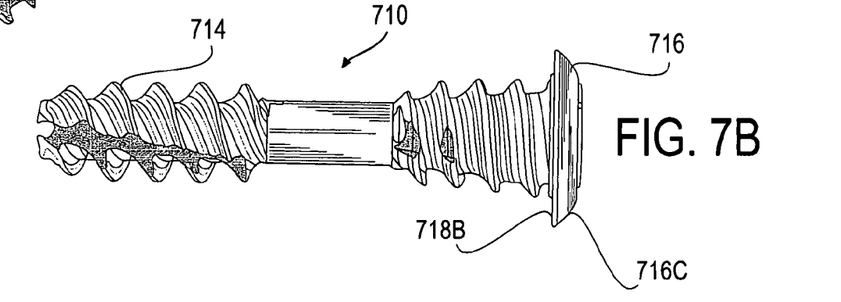

FIGS. 7A and 7B are alternative perspective views of another embodiment of a screw assembly 710. In this embodiment, the screw assembly 710 includes a screw body 714 and a washer 716 that are somewhat similar to the corresponding components described above. In the embodiment, the back side 716B of the washer 716 is generally flat, annular ring shaped and the front side 716C of the washer 716 is arch or tapered shaped. With this design, the relatively flat back side 716B engages the bone region and the curved front side 716C provides a lower profile to reduce potential irritation.

Figure 8A:
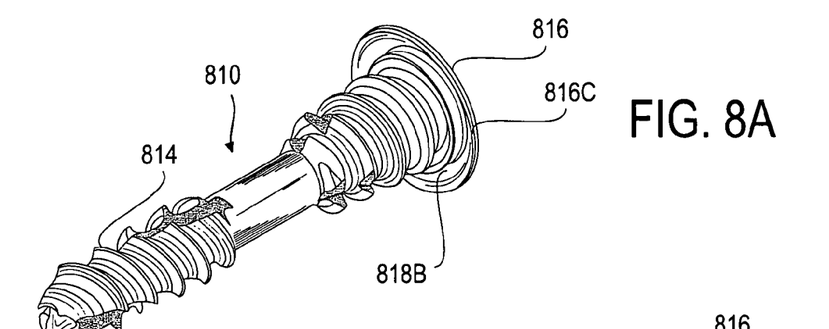
FIGS. 8A and 8B are alternative perspective views of yet another embodiment of a screw assembly having features of the present invention.
Figure 8B:
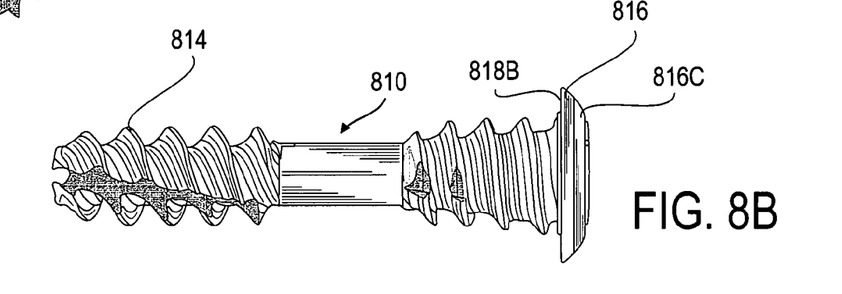

FIGS. 8A and 8B are alternative perspective views of yet another embodiment of a screw assembly 810 having features of the present invention. In this embodiment, the screw assembly 810 includes a screw body 814 and a washer 816 that are somewhat similar to the corresponding components described above. In this embodiment, the back side 816B of the washer 816 is cupped or curved inward and the front side 816C of the washer 816 is arch or tapered shaped. With this design, the back side 816B can provide an area for bone growth into the washer 816, and the curved front side 816C provides a lower profile to reduce potential irritation.

Figure 9A:
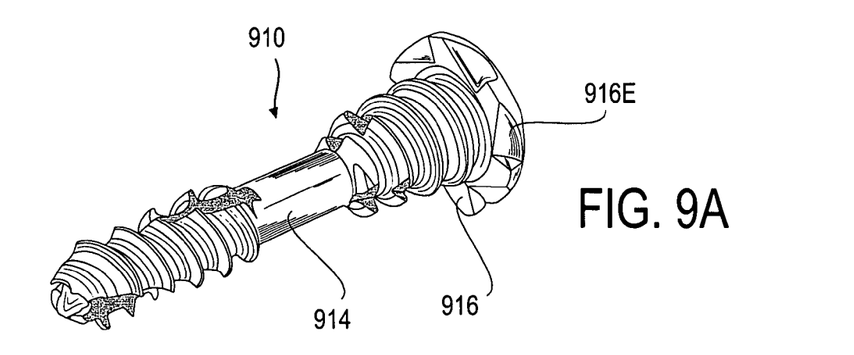
Figure 9B:
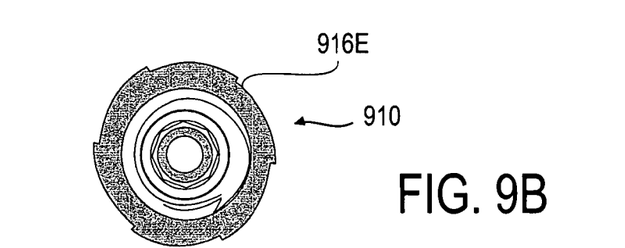
Figure 9C:
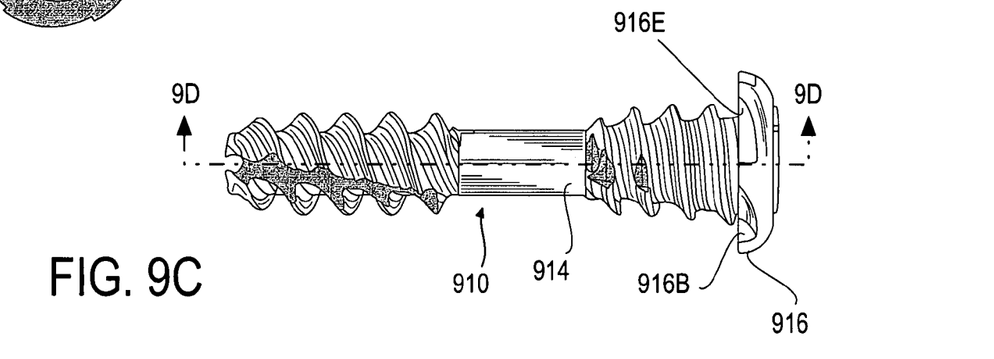
Figure 9D:
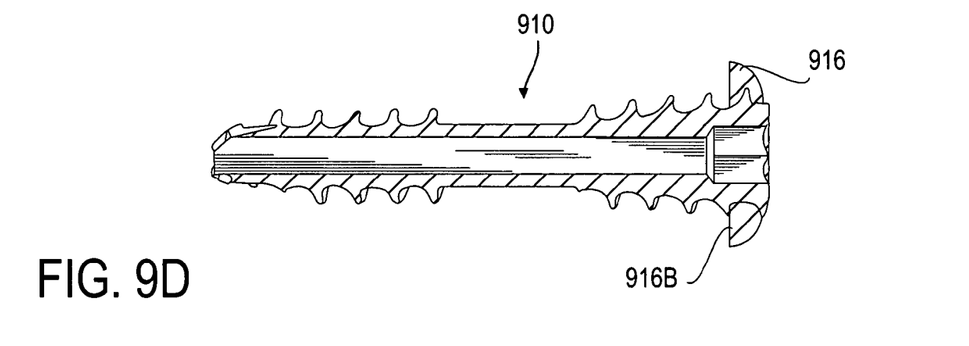
FIG. 9D is a cut-away view of still another embodiment of a screw assembly having features of the present invention.

FIG. 9A is a perspective view, FIG. 9B is an end view, FIG. 9C is a side view, and FIG. 9D is a cut-away view of still another embodiment of a screw assembly 910. In this embodiment, the screw assembly 910 includes a screw body 914 and a washer 916 that are somewhat similar to the corresponding components described above. In this embodiment, the back side 916B includes a plurality of spaced apart washer slots 916E that are spaced apart circumferentially. With this design, the washer slots 916E can be used to cut into the surface of the bone region. This can eliminate the need for a counter bore drill procedure.

Figure 10A:
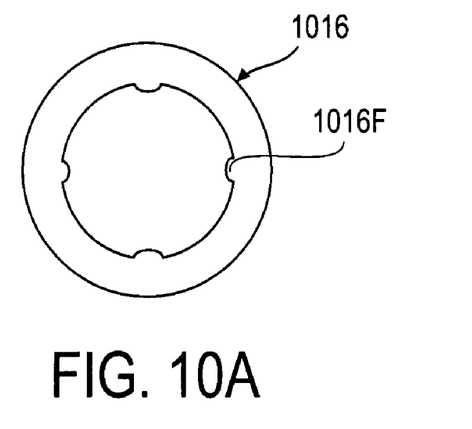
FIGS. 10A-10C are alternative views of a washer having features of the present invention.
Figure 10B:
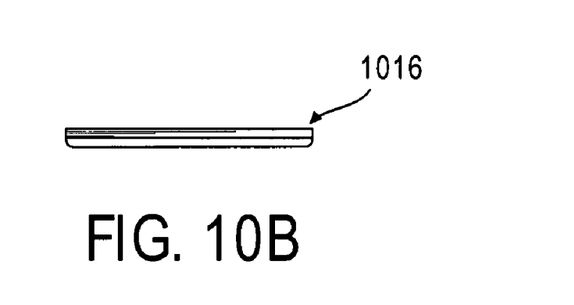
Figure 10C:
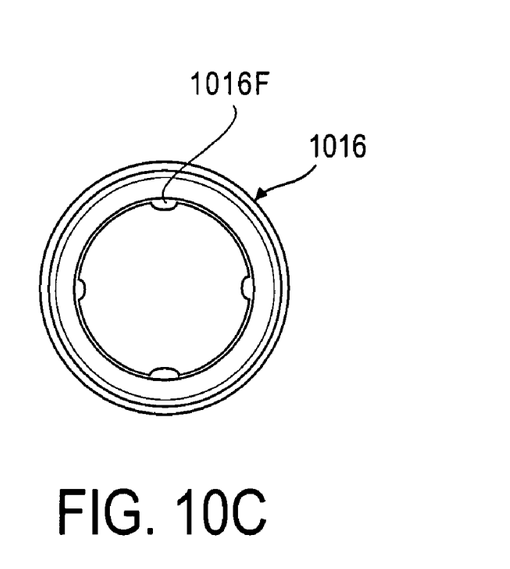

FIGS. 10A-10C are alternative views of a washer 1016 having features of the present invention. In this embodiment, the washer 1016 includes a plurality of spaced apart washer flanges 1016F that extend inward to engage the screw body (not shown) and fixedly secure the washer 1016 to the screw body.

Figure 11A:
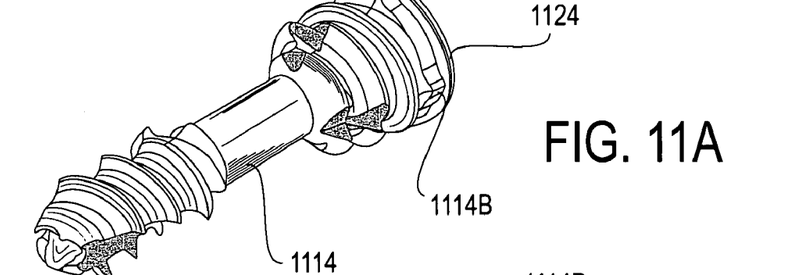
FIGS. 11A and 11B are alternative views of a screw body having features of the present invention.
Figure 11B:
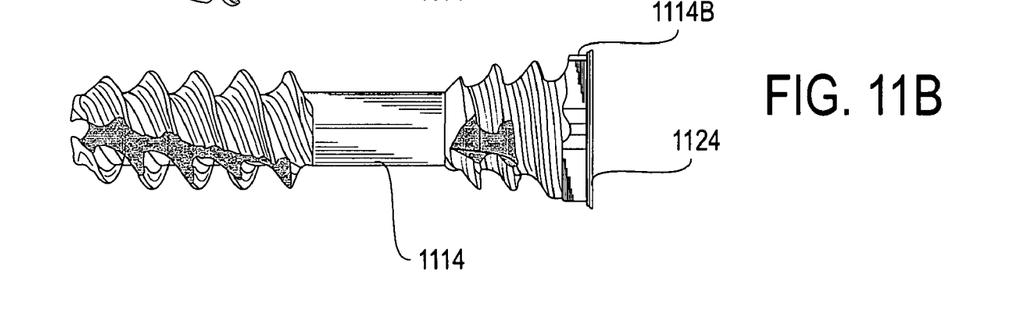

FIGS. 11A and 11B are alternative views of a screw body 1114 having features of the present invention. In this embodiment, the screw body 1114 is somewhat similar to the screw bodies described above. However, in this embodiment, the screw body 1114 includes a plurality of spaced apart screw ribs 1114B that extend outward to engage the washer (not shown). In this embodiment, the screw ribs 1114B are positioned near the proximal end 1124.

Figure 12A:
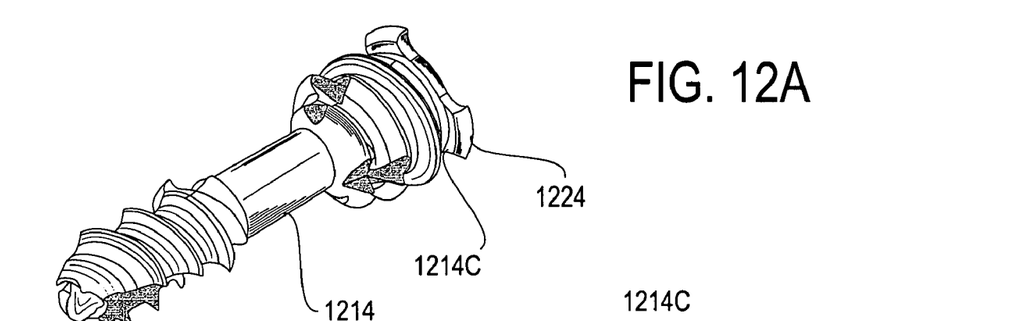
FIGS. 12A and 12B are alternative views of another embodiment of a screw body having features of the present invention.
Figure 12B:
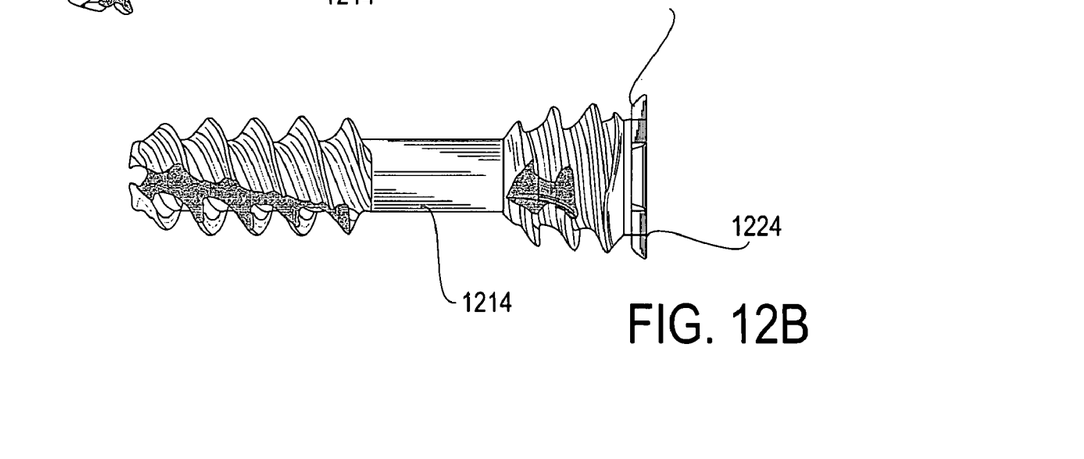

FIGS. 12A and 12B are alternative views of another embodiment of a screw body 1214 having features of the present invention. In this embodiment, the screw body 1214 is somewhat similar to the screw bodies described above. However, in this embodiment, the screw body 1214 includes a circumferential screw slot 1214C that receives the washer (not shown). In this embodiment, the screw slot 1214C is positioned near the proximal end 1124.

While the particular screw assembly 10 as shown and disclosed herein is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A screw assembly for insertion into a bone region, the screw assembly comprising:
    a screw body including a distal end, a proximal end, a proximal threaded area positioned near the proximal end, and a distal threaded area positioned near the distal end; and
    a washer including an internal threaded area configured to engage with the proximal threaded area of the screw body, wherein the washer further includes a first section and a second section, wherein the first section includes a first outer diameter, wherein the second section includes a second outer diameter larger than the first outer diameter, wherein the first and second sections are formed of a single piece, and wherein the second section further includes an interior surface configured to mount flush with an outer surface of the bone region;
    wherein the proximal threaded area includes a bone thread region that is configured to engage the bone region, and a washer thread region that is engaged by the washer threaded area, the threads of the bone thread region being different from the threads of the washer thread region.

2. The screw assembly of claim 1 wherein the proximal threaded area has a length that is greater than a thickness of the washer.

3. The screw assembly of claim 2 wherein the washer is adapted to selectively lock onto the proximal threaded area with a portion of the proximal threaded area exposed for engaging the bone region.

4. The screw assembly of claim 1 wherein the washer includes a washer slit that allows the washer to be slid onto the washer body from a side of the washer body.

5. The screw assembly of claim 1 wherein the washer includes at least one washer tooth adapted to facilitate cutting by the washer into the bone region.

6. The screw assembly of claim 1 wherein the washer includes a washer fill region adapted to provide an area for bone growth from the bone region.

7. The screw assembly of claim 1 wherein at least one of the screw body and the washer includes a tapered area so that washer fixedly engages the screw body.

8. The screw assembly of claim 1, wherein the washer is a first washer, wherein the internal threaded area is a first internal threaded area, and wherein the interior surface is a first interior surface, the screw assembly further comprising:
    a second washer including a second internal threaded area configured to engage with the proximal threaded area of the screw body, wherein the second washer further includes a third section and a fourth section, wherein the third section includes a third outer diameter, wherein the fourth section includes a fourth outer diameter larger than the third outer diameter, and wherein the fourth section further includes a second interior surface larger than the first interior surface and configured to mount flush with the outer surface of the bone region.

9. The screw assembly of claim 8, further comprising:
    a third washer including a third internal threaded area configured to engage with the proximal threaded area of the screw body, wherein the third washer further includes a fifth section and a sixth section, wherein the fifth section includes a fifth outer diameter, wherein the sixth section includes a sixth outer diameter larger than the fifth outer diameter, and wherein the sixth section further includes a third interior surface larger than the second interior surface and configured to mount flush with the outer surface of the bone region.

10. The screw assembly of claim 8,
wherein each of the first and second washers is configured to alternatively and selectively secure to the screw body near the proximal end such that the interior surface of the selected washer mounts flush with an outside surface of the bone region to provide stability and compression.

11. The screw assembly of claim 10 wherein each of the first and second washers is configured to thread onto the screw body.

12. The screw assembly of claim 11 wherein the first internal threaded area is substantially the same as the second internal threaded area a.

13. The screw assembly of claim 10 wherein at least one of the first and second washers includes at least one washer tooth adapted to facilitate cutting by that washer into the bone region.

14. The screw assembly of claim 10 wherein at least one of the first and second washers includes a washer fill region adapted to provide an area for bone growth from the bone region.

15. The screw assembly of claim 10 wherein either or both of the screw body and the first and second washers includes a tapered area so that the washers can be alternatively and selectively secured to the screw body near the proximal end.

16. The screw assembly of claim 1, wherein the threads of the bone thread region have a different thread pitch than the threads of the washer thread region.

* * * * *